(12) United States Patent
Gumm

(10) Patent No.: US 8,211,137 B2
(45) Date of Patent: Jul. 3, 2012

(54) ROTATING STENT DELIVERY SYSTEM FOR SIDE BRANCH ACCESS AND PROTECTION AND METHOD OF USING SAME

(76) Inventor: Darrel C. Gumm, Peoria, IL (US)

(*) Notice: Subject to any disclaimer, the term of this patent is extended or adjusted under 35 U.S.C. 154(b) by 210 days.

(21) Appl. No.: 12/504,608

(22) Filed: Jul. 16, 2009

(65) Prior Publication Data

US 2010/0036390 A1 Feb. 11, 2010

Related U.S. Application Data

(63) Continuation of application No. 10/226,362, filed on Aug. 22, 2002, now Pat. No. 7,563,270.

(60) Provisional application No. 60/314,467, filed on Aug. 23, 2001.

(51) Int. Cl.
*A61M 29/00* (2006.01)

(52) U.S. Cl. ............ 606/194; 604/96.01; 623/1.11

(58) Field of Classification Search ............ 606/192, 606/19, 195; 623/1.11, 1.35; 604/96.01, 604/104, 284, 523

See application file for complete search history.

(56) References Cited

U.S. PATENT DOCUMENTS

| | | | |
|---|---|---|---|
| 4,484,585 A | 11/1984 | Baier |
| 4,601,701 A | 7/1986 | Mueller, Jr. |
| 4,769,005 A | 9/1988 | Ginsburg et al. |
| 4,776,337 A | 10/1988 | Palmaz |
| 4,913,141 A | 4/1990 | Hillstead |
| 4,988,356 A | 1/1991 | Crittenden et al. |
| 4,994,071 A | 2/1991 | MacGregor |
| 4,998,923 A | 3/1991 | Samson et al. |
| 5,019,085 A | 5/1991 | Hillstead |
| 5,209,728 A | 5/1993 | Kraus et al. |
| 5,316,023 A | 5/1994 | Palmaz et al. |
| 5,318,535 A | 6/1994 | Miraki |
| 5,348,537 A | 9/1994 | Wiesner et al. |
| 5,397,305 A | 3/1995 | Kawula et al. |
| 5,449,343 A | 9/1995 | Samson et al. |
| 5,477,856 A | 12/1995 | Lundquist |
| 5,609,627 A | 3/1997 | Goicoechea et al. |
| 5,632,736 A | 5/1997 | Block |
| 5,643,278 A | 7/1997 | Wijay |
| 5,693,015 A | 12/1997 | Walker et al. |
| 5,697,971 A | 12/1997 | Fischell et al. |
| 5,720,735 A | 2/1998 | Dorros |
| 5,725,519 A | 3/1998 | Penner et al. |
| 5,749,825 A | 5/1998 | Fischell et al. |

(Continued)

FOREIGN PATENT DOCUMENTS

DE 29701758 3/1997

(Continued)

OTHER PUBLICATIONS

Foley et al., "Bifurcation Lesion Stenting," The Thoraxcentre Journal, vol. 8, No. 4, pp. 32-35, 1998.

(Continued)

*Primary Examiner* — Tuan Nguyen
(74) *Attorney, Agent, or Firm* — Seager Tufte & Wickhem LLC

(57) ABSTRACT

A catheter assembly and method of use comprises advancing a catheter having a rotatably mounted balloon relative to the primary guide wire to a vessel bifurcation along first and second guide wires.

15 Claims, 6 Drawing Sheets

U.S. PATENT DOCUMENTS

| | | | |
|---|---|---|---|
| 5,755,735 A | 5/1998 | Richter et al. | |
| 5,797,952 A | 8/1998 | Klein | |
| 5,824,055 A | 10/1998 | Spiridigliozzi et al. | |
| 5,873,906 A | 2/1999 | Lau et al. | |
| 5,876,374 A | 3/1999 | Alba et al. | |
| 5,906,640 A | 5/1999 | Penn et al. | |
| 5,908,405 A | 6/1999 | Imran et al. | |
| 5,921,995 A | 7/1999 | Kleshinski | |
| 5,961,548 A | 10/1999 | Shmulewitz | |
| 6,027,460 A | 2/2000 | Shturman | |
| 6,033,434 A | 3/2000 | Borghi | |
| 6,048,361 A | 4/2000 | Von Oepen | |
| 6,056,722 A | 5/2000 | Jayaraman | |
| 6,056,775 A | 5/2000 | Borghi et al. | |
| 6,071,286 A | 6/2000 | Mawad | |
| 6,096,073 A | 8/2000 | Webster et al. | |
| 6,099,497 A | 8/2000 | Adams et al. | |
| 6,110,191 A | 8/2000 | Dehdashtian et al. | |
| 6,117,156 A | 9/2000 | Richter et al. | |
| 6,143,014 A | 11/2000 | Dehdashtian et al. | |
| 6,165,195 A | 12/2000 | Wilson et al. | |
| 6,190,360 B1 | 2/2001 | Iancea et al. | |
| 6,210,380 B1 | 4/2001 | Mauch | |
| 6,210,431 B1 | 4/2001 | Power | |
| 6,221,090 B1 | 4/2001 | Wilson | |
| 6,224,587 B1 | 5/2001 | Gibson | |
| 6,246,914 B1 | 6/2001 | de la Rama et al. | |
| 6,254,593 B1 | 7/2001 | Wilson | |
| 6,258,073 B1 | 7/2001 | Mauch | |
| 6,280,466 B1 | 8/2001 | Kugler et al. | |
| 6,287,330 B1 | 9/2001 | Johansson et al. | |
| 6,290,673 B1 | 9/2001 | Shanley | |
| 6,302,906 B1 | 10/2001 | Goicoechea et al. | |
| 6,319,275 B1 | 11/2001 | Lashinski et al. | |
| 6,322,548 B1 | 11/2001 | Payne et al. | |
| 6,352,561 B1 | 3/2002 | Leopold et al. | |
| 6,361,544 B1 | 3/2002 | Wilson et al. | |
| 6,361,555 B1 | 3/2002 | Wilson | |
| 6,371,978 B1 | 4/2002 | Wilson | |
| 6,375,660 B1 | 4/2002 | Fischell et al. | |
| 6,379,372 B1 | 4/2002 | Dehdashtian et al. | |
| 6,387,120 B2 | 5/2002 | Wilson et al. | |
| 6,406,489 B1 | 6/2002 | Richter et al. | |
| 6,436,104 B2 | 8/2002 | Hojeibane | |
| 6,475,166 B1 | 11/2002 | Escano | |
| 6,488,694 B1 | 12/2002 | Lau et al. | |
| 6,508,835 B1 | 1/2003 | Shaolian et al. | |
| 6,514,281 B1 | 2/2003 | Blaeser et al. | |
| 6,520,988 B1 * | 2/2003 | Colombo et al. | 623/1.35 |
| 6,533,805 B1 | 3/2003 | Jervis | |
| 6,540,719 B2 | 4/2003 | Bigus et al. | |
| 6,589,262 B1 | 7/2003 | Honebrink et al. | |
| 6,596,020 B2 | 7/2003 | Vardi et al. | |
| 6,599,315 B2 | 7/2003 | Wilson | |
| 6,607,506 B2 | 8/2003 | Kletschka | |
| 6,629,981 B2 | 10/2003 | Bui et al. | |
| 6,669,718 B2 | 12/2003 | Besselink | |
| 7,225,518 B2 | 6/2007 | Eidenschink et al. | |
| 7,314,480 B2 | 1/2008 | Eidenschink et al. | |
| 7,367,989 B2 | 5/2008 | Eidenschink | |
| 7,563,270 B2 * | 7/2009 | Gumm | 606/194 |
| 2001/0049548 A1 | 12/2001 | Vardi et al. | |
| 2002/0019664 A1 | 2/2002 | Douglas | |
| 2002/0019665 A1 | 2/2002 | Dehdashtian et al. | |
| 2002/0072755 A1 * | 6/2002 | Bigus et al. | 606/108 |
| 2003/0033001 A1 | 2/2003 | Igaki | |
| 2003/0055484 A1 | 3/2003 | Lau et al. | |
| 2003/0130716 A1 | 7/2003 | Weber et al. | |
| 2005/0149161 A1 | 7/2005 | Eidenschink et al. | |
| 2005/0154442 A1 | 7/2005 | Eidenschink et al. | |
| 2005/0182473 A1 | 8/2005 | Eidenschink et al. | |
| 2005/0273149 A1 | 12/2005 | Tran et al. | |

FOREIGN PATENT DOCUMENTS

| | | |
|---|---|---|
| FR | 2678508 | 1/1993 |
| WO | 03017872 | 3/2003 |
| WO | 03055414 | 3/2003 |

OTHER PUBLICATIONS

Nakamura et al., "Techniques for Palmaz-Schatz Stent Deployment in Lesions with a Large Side Branch," Catheterization and Cardiovascular Diagnosis, vol. 34, pp. 353-361, 1995.

Oda et al., ""Fork" Stenting for Bifurcational Lesion," vol. 9, No. 6, pp. 445-454, 1996.

Palmaz et al., "Aortic Bifurcation Stenosis: Treatment with Intravascular Stents," Journal of Vascular and Interventional Radiology, vol. 2, No. 3, pp. 319-323, Aug. 1991.

Pomerantz et al., "Distortion of Palmaz-Schatz Stent Geometry Following Side-Branch Balloon Dilation Through the Stent in a Rabbit Model," Catheterization and Cardiovascular Diagnosis, vol. 40, pp. 422-426, 1997.

Schampaert et al., "The V-Stent: A Novel Technique for Coronary Bifurcation Stenting," Catheterization and Cardiovascular Diagnosis, vol. 39, pp. 320-326, 1996.

* cited by examiner

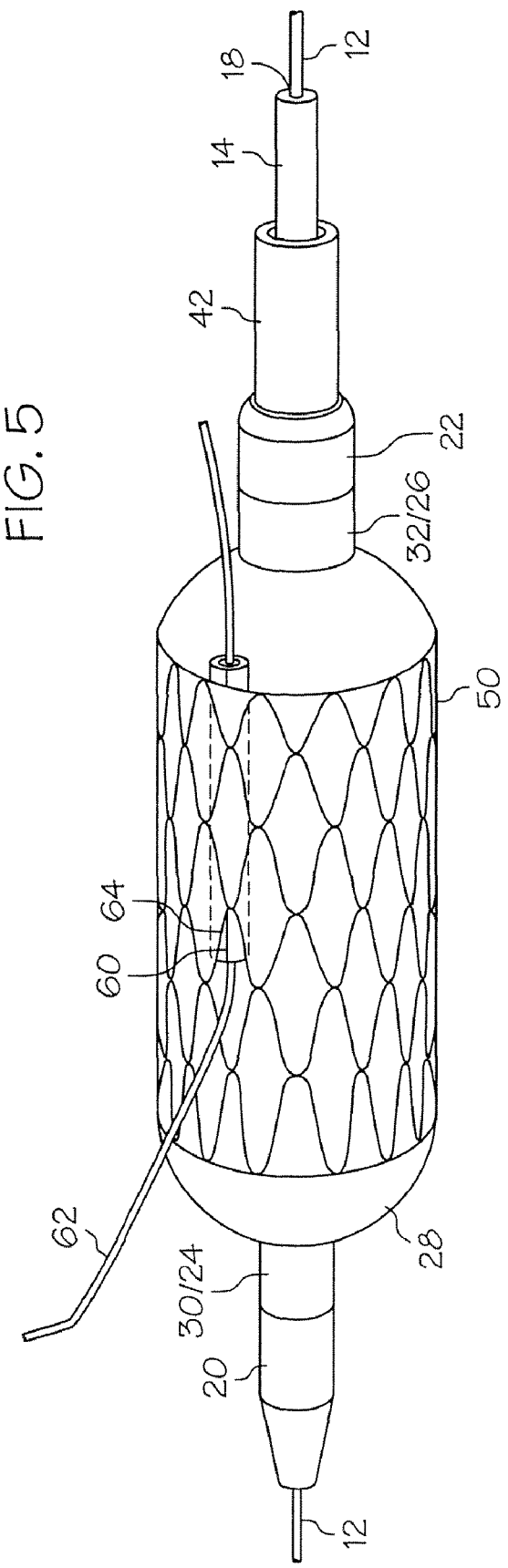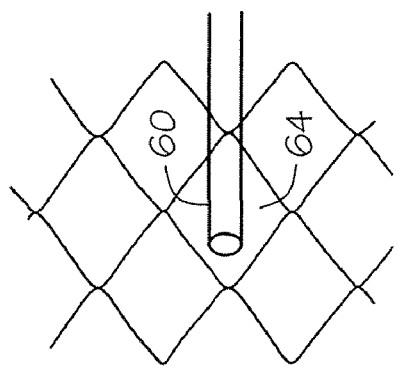

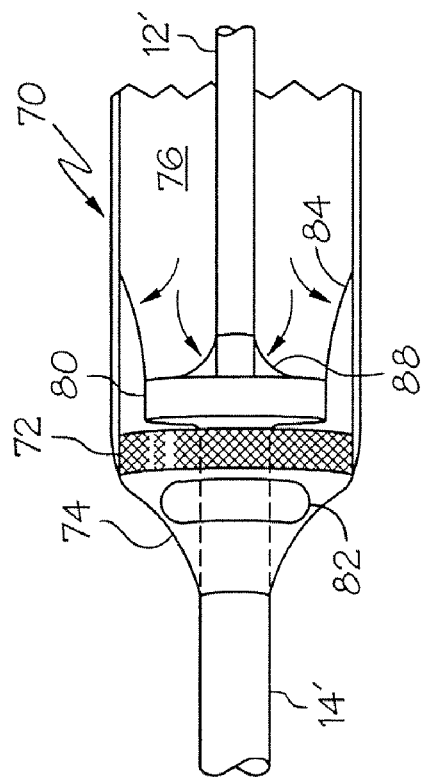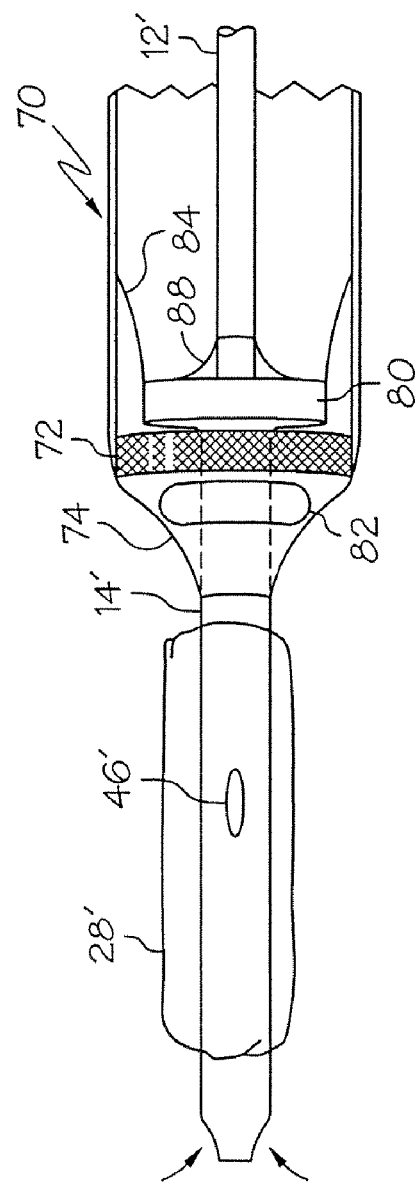

ROTATING STENT DELIVERY SYSTEM FOR SIDE BRANCH ACCESS AND PROTECTION AND METHOD OF USING SAME

CROSS-REFERENCE TO RELATED APPLICATIONS

This application is a continuation of U.S. application Ser. No. 10/226,362, filed Aug. 22, 2002, which is now U.S. Pat. No. 7,563,270, titled "ROTATING STENT DELIVERY SYSTEM FOR SIDE BRANCH ACCESS AND PROTECTION AND METHODS OF USING", which claims priority to U.S. Provisional Application 60/314,467, filed Aug. 23, 2001, all of which are hereby incorporated by reference in their entirety.

BACKGROUND OF THE INVENTION

1. Field of the Invention

At least one embodiment of the present invention is directed to the field of stents and stent delivery systems used to treat stenoses, and more particularly to stenoses at a bifurcation of a passage

2. Description of the Related Art

Stent systems are widely used in the treatment of stenoses. Intravascular stents are used in coronary, renal, and carotid arteries, for example, to maintain an open passage through the artery. In patients whose coronary heart disease consists of focal lesions, stents have proven effective. For example, where only a single coronary artery is clogged or where there are short blockages in more than a single artery, stents have been used with a great amount of success. An intravascular stent may be positioned in a clogged artery by a catheter and is often set in place by inflating a balloon upon which the stent is mounted. This expands the diameter of the stent and opens the previously clogged artery. The balloon is then deflated and removed from the patient while the stent retains an open passage through the artery.

It is recognized, however, that a stent can be deployed in manners other than inflating and deflating a balloon. For example, self-expanding stents have been developed in which a cover is removed from over a stent, thereby allowing the stent to deploy or spring into place. It is also contemplated that other deployment mechanisms or means may be used or developed to advantageously deliver and deploy a stent in position.

Nevertheless, a need still exists for properly delivering and locating a stent at a bifurcation. Although efforts have been made to use a stent at bifurcations, these sites have previously been inadequately treated by a stent. For example, U.S. Pat. No. 5,749,825 is representative of a catheter system that treats stenoses at an arterial bifurcation. The disclosure of U.S. Pat. No. 5,749,825 is hereby incorporated by reference.

A stent having different diameters has been proposed to allow placement in both a main passage, such as an artery, and a side branch passage, such as a continuation branch artery. Additionally, these stents generally have a circular opening which allows for unimpeded blood flow into the side branch artery. However, problems are still encountered in orienting the stent relative to the side branch at the bifurcation of the main and branch passages.

Many current devices rely on either passive torque (e.g., pushing the stent forward and allowing the stent that is fixed on the guide wire/balloon to passively rotate itself into place) or creating torque from outside of the patient to properly orient the stent delivery system in the passage. These devices and methods of achieving proper angular orientation have not been shown to be effective in properly placing and positioning the stent. As will be appreciated and understood by those skilled in the art, improper placement of the stent with respect to its rotational or circumferential orientation, or its longitudinal placement, could lead to obstruction of the side branch passage. It is important to properly position or center an opening formed in the bifurcated stent with the side branch passage to maximize flow therethrough.

Thus, a need exists for effectively treating stenosed passage bifurcations. This need includes more precise and exact longitudinal placement and rotational/circumferential orientation of the stent.

Commercially available devices do not maintain side branch access at the time of stent deployment. This results in the potential for plaque shift and occlusion of the side branch passage.

It would also be advantageous if stents could be placed across the side branch while wire position is maintained thereby helping to protect and secure further access to the side branch.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

Some embodiments of the present invention include a freely rotating deployment system for a stent assembly maintaining side branch access and protection.

The present invention contemplates a new and improved apparatus and method that improves the orientation of a stent by providing a more exact placement of the stent relative to the side branch passage. This, in turn, may lead to better protection of the side branch passage. The present invention has the potential for improvement in trackability of the stent delivery system.

In one illustrative embodiment, a method of delivering a medical device to a bifurcated vessel is disclosed. The method may include advancing the medical device over a first guidewire and/or a second guidewire to a bifurcation in a vessel. In some embodiment, the medical device may include a balloon that may be rotatable or selectively rotatable about a shaft of the medical device during at least a portion of the advancing. The balloon may also be selectively sealable to the shaft of the medical device, which in some cases, may be when the medical device reaches a desired location in the vessel.

In at least one embodiment, the medical device may include a freely rotatable catheter balloon surrounding a main hollow member or hypotube. A stent may surround both the catheter balloon and the main hypotube. In some cases, a side branch hollow member or side branch hypotube is attached to the catheter balloon and lies underneath the stent. A distal end of the side branch hypotube may exit the stent at a desired longitudinal position while a proximal end of the side branch hypotube extends beyond the proximal end of the stent.

A feature of some embodiments may be that at the time of positioning the stent, the stent will be properly oriented relative to the side branch, i.e., a stent delivery system and method that correctly positions the stent in a bifurcated passage.

Another feature may be side branch protection with the guide wire during stent deployment.

Another feature may be proper alignment of the stent delivery system in a bifurcated passage to achieve correct circumferential orientation relative to a side branch passage, and securing the desired orientation.

Yet another feature may be the ability to properly place the stent delivery system longitudinally relative to the side branch.

A further feature may be that tangled wires pose less of a problem. These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

FIG. 2 is a perspective view of the stent delivery assembly of FIG. 1 shown with a stent disposed about the balloon.

FIG. 5 is an enlarged view of the distal exit point of the side branch hypotube and the opening of the rotating stent delivery catheter assembly of FIG.

FIG. 8 is an enlarged side view of the combined components of FIGS. 6 and 7, specifically portions of the distal end of the proximal fixed shaft in FIG. 6 combined with the proximal end of the freely rotatable distal portion in FIG. 7 creating a rotating stent delivery catheter assembly with a single rotating joint that is self sealing.

FIG. 9 is an enlarged side elevational view of FIGS. 6 and 7 showing the combined of components of FIGS. 6-8 in their entirety.

DETAILED DESCRIPTION OF THE INVENTION

Figure 1:
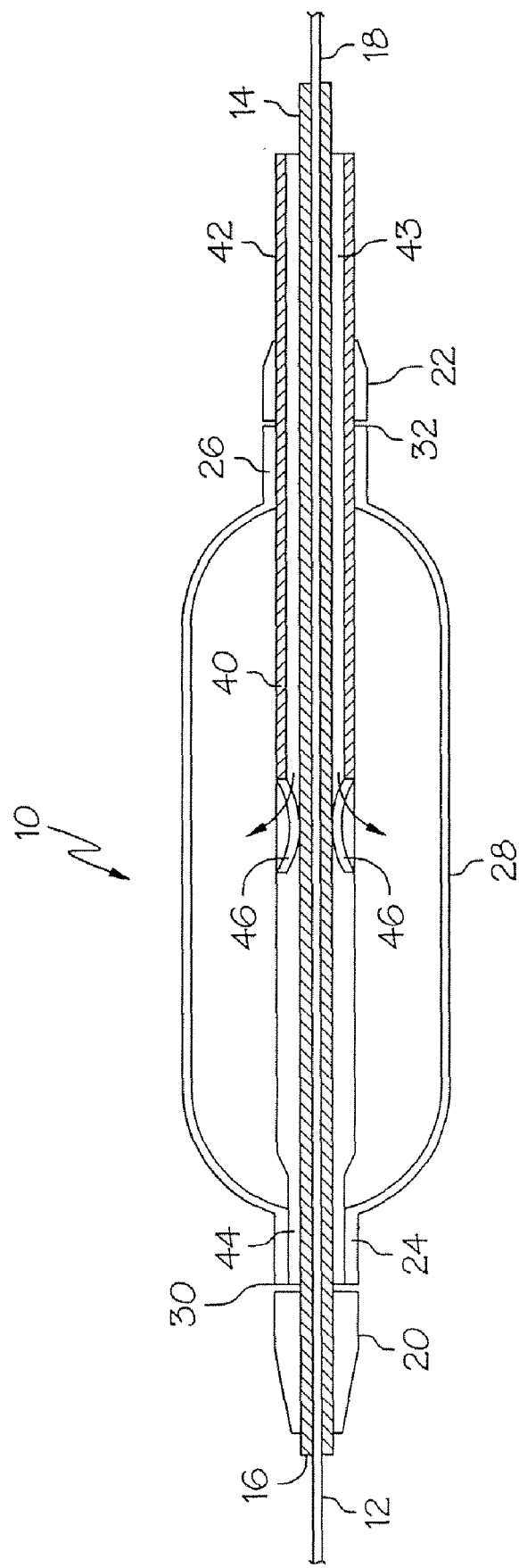
FIG. 1 is a cross-sectional side view of a rotating stent delivery catheter assembly for stenting an arterial bifurcation in its pre-deployment configuration, with the catheter balloon shown inflated.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Referring now to the drawings wherein the showings are for the purposes of illustrating the preferred embodiments of the invention only and not for purposes of limiting same, FIG. 1 shows a stent delivery system or assembly 10. Assembly 10 includes a first guide member, or main guide wire 12 that extends axially through a first hollow or tubular member 14. The first hollow member 14 will also be identified as a main hypotube, although it will be appreciated that the particular shape or configuration of this component may change from that illustrated in the drawings. The main guide wire 12 is used as the delivery guide of the stent catheter assembly 10 to a stenosed region of a passage such as an artery (not shown). The main hypotube 14 is preferably a hollow cylinder with openings on both its distal and proximal ends, respectively end 16 and end 18, which allows for passage of the main guide wire 12 therethrough. A first fixed member, or distal fixed body 20 and a second fixed member, or proximal fixed body 22 are non-rotatably secured to distal end 16 and proximal end 18 of the main hypotube 14. Although described as separate elements, it will be understood that the fixed bodies 20 and 22 and the main hypotube 14 can be separate components that are secured together or an integrally formed assembly if desired for ease of manufacture or assembly. The fixed bodies 20 and 22 are preferably tapered from smaller diameter, axially outer ends to larger diameter, intermediate ends for reasons that will become more apparent below.

A first rotating member or distal rotating member 24 and a second rotating member or proximal rotating member 26 are axially spaced apart and located between the distal fixed body 20 and proximal fixed body 22. The rotating members 24 and 26 are preferably of the same general diameter throughout their length and rotate freely about the axis of the main hypotube 14.

Sealed to the proximal and distal rotating members 24 and 26 are opposite ends of a catheter balloon 28. A distal end 30 of the catheter balloon is sealingly joined to (or integrally formed with) the distal rotating member 24 while a proximal end 32 of the catheter balloon is sealingly joined to (or integrally formed with) the proximal rotating member 26. Thus, the balloon is free to rotate relative to the main hypotube, a feature that provides advantages and benefits over known stent assemblies. It is also contemplated that the rotating members 24 and 26 can be formed of sealing or elastomeric material (or incorporate a separate seal member) so that slight axial movement of the balloon 28 and of the rotating members 24 and 26 engages and seals against the fixed bodies 20 and 22 upon inflation of the balloon 28. The balloon 28 and the rotating members 24 and 26 can hold high pressure and seal at the ends. It will be appreciated that the rotating members 24 and 26 are preferably constructed to maintain a cylindrical configuration under pressure so that the balloon 28 is free to rotate relative to the main hypotube 14 when pressurized.

In some embodiments the stent delivery catheter system further includes an outer hollow/tubular member or outer hypotube 40 received over the main hypotube 14. The outer hypotube 40 is radially spaced from the main hypotube 14 at a first or proximal end 42 to define an annular space 43 through which fluid from an external source (not shown) is introduced to inflate the balloon. In at least one embodiment, a second or distal end 44 of the outer hypotube 40 is sealed to the main hypotube 14 so that fluid cannot escape therefrom. Alternatively, the distal end of the outer hypotube extends only partially into the balloon 28. In addition, one or more openings, or contrast ports, 46 are provided in the outer hypotube 40 at a location within the balloon 28 so that the fluid can enter the cavity defined between the balloon 28 and the outer hypotube 40 as illustrated by the directional arrows in FIG. 1. Alternatively, the opening 46 may define the distal end of the outer hypotube 40. In at least one embodiment, the balloon 28 is fully inflated at the proximal end 42 and then begins to inflate at the distal end 44. The outer hypotube 40 may be advantageously and integrally formed with the first and second fixed members 20 and 22 for ease of manufacture, although it will be appreciated that these may be separate members without departing from the scope and intent of the invention.

A conventional or specially designed medical device, such as a stent 50, encloses a portion of the catheter balloon 28, such as is shown in FIG. 2. The stent 50 is typically a metal sleeve of mesh construction that is advanced into the stenosis riding on the balloon 28 of the catheter assembly 10. Once properly positioned, the balloon 28 is inflated with an inflation fluid, such as saline and contrast, through the passage 43 between the main hypotube 14 and the outer hypotube 40, which expands the balloon 28 and expands or radially opens the stent 50 to compress an atheroma that is narrowing the passage wall. Although the balloon 28 is subsequently deflated for removal from the patient with the catheter assembly 10, the stent 50 remains in its expanded state allowing increased flow through the previously closed/blocked (stenosed or narrowed) region. Alternatively, a self-expanding stent not requiring a balloon for delivery or deployment can be used without departing from the scope and intent of the present invention.

A second or branch tubular member 60, also referred to as a side branch hypotube, is provided between the catheter balloon 28 and the stent 50. As evident in FIG. 2, the side branch hypotube 60 carries or receives a side branch guide wire 62. The side branch hypotube 60 extends from the proximal end of the stent 50 between the stent and balloon and exits the stent at an intermediate longitudinal position through an opening 64. The opening 64 provides for both the exit of the side branch hypotube 60, as well as the unobstructed passage of blood flow into the side branch passage once the stent has been deployed. It should be understood, however, that the side branch hypotube opening 64 could be placed at any convenient position along the stent.

An enlarged view of the side branch hypotube opening 64 in the stent 50 is shown in FIG. 5. The side branch hypotube 60 exits from underneath the proximal end of the stent. Upon deployment of the stent 50, the side branch hypotube opening 64 allows for unobstructed blood flow to the ostium of the side branch passage. As will also be appreciated, the side branch hypotube 60 is fixed or secured to the exterior of the balloon. Thus, the side branch hypotube 60, balloon 28, and rotating members freely rotate as a unit relative to the main hypotube 14 for accurate, passive positioning with the side guide wire and thus accurate positioning of the stent 50 relative to a saddle point of the bifurcated passage. With continued reference to FIG. 2, the catheter balloon 28 is inflated, the stent 50 is deployed, and the rotating members 24 and 26 are interlocked with the fixed members 20 and 22 to stop the rotating action of the stent delivery system and create a pressure tight system.

Figure 3:
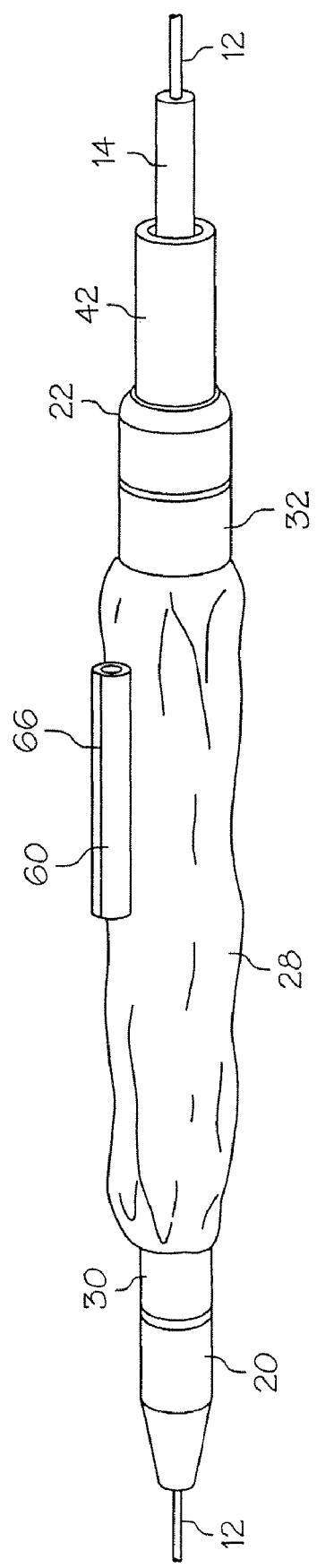
FIG. 3 is a perspective view of the stent delivery catheter assembly of FIG. 1 as it would appear in the collapsed state prior to having a stent mounted on the balloon.
Figure 4:
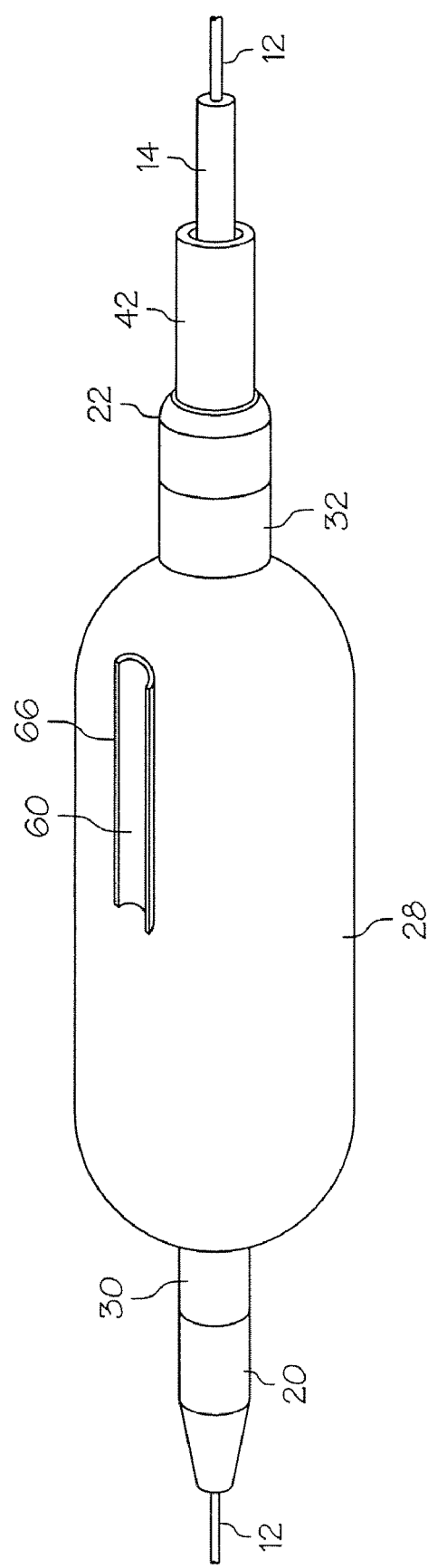
FIG. 4 is a perspective view of a stent delivery system with the balloon in an inflated state and the side branch hypotube in an open condition.
Figure 6:
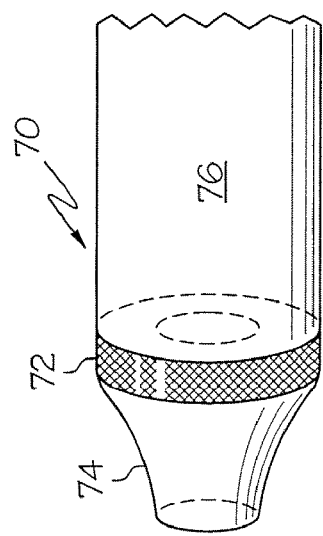
FIG. 6 is a perspective view of a proximal shaft of an alternate stent delivery catheter assembly having only one rotating joint that is self sealing when pressure is applied or withdrawn.

The side branch hypotube 60 may also be slit 66 along its longitudinal length to facilitate removal of the side guide wire 62 as is shown in FIGS. 3 and 4. The side branch hypotube 60 is secured to the balloon 28 along its length at a circumferential location opposite the longitudinal slit, i.e., diametrically opposite the slit 66. The natural elasticity of the side branch hypotube 60 is utilized so that when the balloon 28 is inflated, such as is shown, the side branch hypotube 60 is substantially cylindrical in shape to enclose the portion of the side guide wire 62 therein such as is shown in FIG. 2. When the balloon is inflated, it exerts a tensile force on the side branch hypotube 60 that opens the hypotube 60 along its length, such as in the manner shown in FIG. 4. As a result the side guide wire 62 is released through the slit 66. When the balloon 28 is deflated, such as is shown in FIG. 3, the side branch hypotube 60 again adopts a cylindrical conformation whereby the remainder of the stent delivery system (balloon and catheter) can be easily removed.

The split side branch hypotube 60 offers another desirable feature. The split hypotube 60 allows for immediate placement of a second balloon into the side branch for simultaneous "kissing" balloon inflation. In other words, first and second balloons are simultaneously located in the main and side branch passages such that their proximal ends abut and their distal ends are placed in each respective branch. This is to be contrasted with use of an unsplit or solid side branch hypotube which would require removal of the first balloon prior to insertion of a balloon in the side branch.

An alternative rotating stent delivery system is illustrated in FIGS. 6-9. For purposes of brevity, like components will be referenced by like numerals with a primed suffix (') and new elements will be identified by new numerals.

A proximal shaft is generally well known in the art and may take numerous forms; however, the proximal shaft 70 shown in FIGS. 6-9 preferably includes a bushing 72 at a distal end and a seal 74 comprised of a soft material. The seal 74 is connected to the proximal shaft 70 and, as shown, tapers to a smaller diameter and envelops the main hypotube 14', as is shown in FIGS. 8 and 9. Within lumen 76 of the proximal shaft 70, the bushing 72 abuts against an interior distal end of the proximal shaft.

Figure 7:
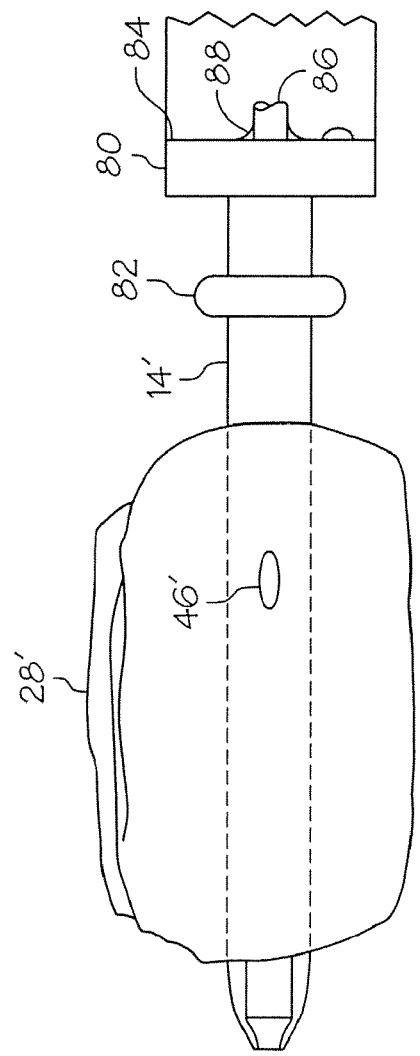
FIG. 7 is an enlarged side view of a distal end of the rotating balloon assembly associated with FIG.

With reference now to FIG. 7, a distal rotating portion of proximal shaft 70 is shown. A separate hypotube 14' includes a proximal end with a first bushing 80 and a second bushing 82 axially spaced therefrom along the separate hypotube 14'. A second seal 84 comprised of a soft material, is connected to the first bushing 80 at the proximal end of the separate hypotube 14'. The annular second seal 84 protrudes substantially parallel along the longitudinal axis of the main hypotube and extends axially beyond an opening 86 for the main branch guide wire (not shown). Additionally, a third annular seal 88 is shown connected to the first bushing 80. The third seal 88 has a smaller diameter and lies axially and radially inward of 5 the second seal 84. The third seal 88 is also secured to the first bushing 80 of the separate hypotube 14' and tapers radially inward as it extends longitudinally in a direction away from the separate hypotube 14', to envelope the main guide wire 12'.

The integration of the proximal end of the separate hypotube 14' and the distal end of the proximal shaft 70 is shown in FIG. 8. Particularly, the first and second bushings 80, 82 of the hypotube 14' are of a diameter that allows them to fit under or within the particular components of the proximal shaft 70. Specifically, the second bushing 82 of the hypotube 14' is distal to the proximal shaft bushing 72 and is enveloped by the first soft seal 74 of the proximal shaft 70. The first bushing 80 of the hypotube 14' is adjacent to the bushing 72 of the proximal shaft and is enveloped by the proximal shaft 70.

With continued reference to FIG. 8, the integrated hypotube 14' and proximal shaft 70 are shown in a freely rotatable position. In this mode, the hypotube 14' rotates freely while the proximal shaft 70 remains fixed. Positive pressure allows the seals 82 and 88 extending from the first bushing 80 of the hypotube 14', to contact the proximal fixed shaft 70 and main guide wire 12' hence sealing the balloon delivery system 10' allowing for all positive pressure to be transferred to the balloon 28'. This provides for expansion of the balloon 28' and deployment of a stent such as previously described. Alternatively, as is shown in FIG. 9 negative pressure applied within the shaft 70 will create contact between the separate hypotube and the seal 74 of the proximal shaft 70. Also, contact will be created at the distal end of the separate hypotube between the soft material and the wire 12' creating a seal there as well. These seals allow for all negative pressure to be transmitted to the balloon allowing for collapse and then removal of the balloon.

Thus, it is apparent that a truly unique feature of the invention is a freely rotating stent assembly that provides a more exact placement of the stent relative to the side branch passage.

The invention has been described with reference to the preferred embodiments. Obviously, modifications and alterations will occur to others upon a reading and understanding of this specification. For example, the illustrated embodiments use a balloon to expand the stent although, as briefly noted above, a self expanding or self deploying stent can be used without departing from the features of the present invention. Likewise, using a fixed wire on the distal end of the apparatus is also recognized as being consistent with the features of the present invention. Moreover, the preferred embodiments describe a side branch hypotube, either split or unsplit, that is associated with the side branch guide wire. It will be further appreciated that the side branch guide wire could be carried and/or released in a variety of other ways. The invention is intended to include all such modifications and alterations thereof.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A method of delivering a medical device to a bifurcated vessel, the method comprising:
    providing a medical device including a catheter shaft defining a first guidewire lumen, a balloon disposed about a portion of a distal region of the catheter shaft, and a side branch tubular member defining a second guidewire lumen and coupled to a portion of the balloon, the balloon including a proximal waist and a distal waist being selectively rotatable about the distal region of the catheter shaft;
    advancing the medical device over a first guidewire and a second guidewire to a bifurcation in a vessel, wherein the first guidewire is received in the first guidewire lumen and the second guidewire is received in the second guidewire lumen, allowing the balloon to passively rotate about the catheter shaft; and
    after advancing the medical device over the first guidewire and a second guidewire, sealing the balloon to the catheter shaft;
    wherein the catheter shaft includes a proximal fixed body and a distal fixed body;
    wherein the proximal waist engages the proximal fixed body and the distal waist engages the distal fixed body when the balloon is sealed.

2. The method of claim 1 wherein axial movement of the balloon relative to the proximal fixed body and distal fixed body seals the balloon.

3. The method of claim 2 wherein at least one of the proximal waist, distal waist, proximal fixed body, and distal fixed body includes an elastomeric material.

4. The method of claim 1 further comprising:
    disposing a stent about a portion of the balloon; and
    expanding the balloon to radially expand and deploy the stent at the bifurcation.

5. The method of claim 1 further comprising advancing a second balloon along the second guidewire so that the medical device and the second balloon are simultaneously located at the bifurcated vessel.

6. The method of claim 4 wherein side branch tubular member includes a slit along the length thereof.

7. A method of delivering a stent to a bifurcation of a vessel, the method comprising:
    advancing a first guidewire through a body lumen to a first branch of a vessel bifurcation;
    advancing a second guidewire through the body lumen to a second branch of the vessel bifurcation;
    advancing a catheter assembly to the vessel bifurcation along the first guidewire and a second guidewire, the catheter assembly comprising:
        a catheter shaft defining a first guidewire lumen for receiving the first guidewire;
        a balloon rotatably disposed about the catheter shaft, the balloon being freely rotatable about the first guidewire;
        a tubular member engaged to an external surface of the balloon, the tubular member defining a second guidewire lumen for receiving the second guidewire; and
        a stent, the stent being disposed about at least a portion of the balloon and the tubular member, the second guidewire passing through at least one opening defined by the stent; and
    sealing the balloon to the catheter shaft by relative axial movement of the balloon and the catheter shaft.

8. The method of claim 7 wherein the relative axial movement is caused by inflating the balloon.

9. The method of claim 7 further comprising advancing a second balloon to the vessel bifurcation along the second guidewire such that the catheter assembly and the second balloon are simultaneously located at the vessel bifurcation.

10. The method of claim 9 wherein tubular member includes a slit along the length thereof for removal of the second guidewire from the second guidewire lumen.

11. A method of delivering a stent to a vessel bifurcation, the method comprising:
inserting a first guidewire into a main branch of the vessel bifurcation;
inserting a second guidewire into a side branch of the vessel bifurcation;
advancing a catheter assembly over the first guidewire and the second guidewire, the catheter assembly including a balloon rotatably disposed about a catheter shaft and a tubular member coupled to an exterior surface of the balloon, the catheter shaft including a first guidewire lumen and the tubular member including a second guidewire lumen, the balloon having a stent disposed thereon, wherein the balloon passively rotates about the catheter shaft as the catheter assembly is advanced over the first guidewire and the second guidewire to properly orient the stent relative to the vessel bifurcation;
inflating the balloon to deploy the stent; and
releasing the side branch guide wire in response to inflating the balloon.

12. The method of claim 11 further comprising releasably sealing the balloon to the catheter shaft.

13. The method of claim 11 wherein the releasing the second guidewire includes opening a slit in the tubular member.

14. The method of claim 11 further comprising advancing a second balloon to the vessel bifurcation along the second guidewire such that the catheter assembly and the second balloon are simultaneously located at the vessel bifurcation.

15. The method of claim 12 wherein the releasably sealing includes engaging at least one elastomeric members of the balloon to one or more fixed bodies of the catheter shaft.

* * * * *